United States Patent [19]

Fey et al.

[11] Patent Number: 4,973,598
[45] Date of Patent: Nov. 27, 1990

[54] SUBSTITUTED IMIDAZOLINONES AND IMIDAZOLINETHIONES

[75] Inventors: Peter Fey; Rolf Angerbauer; Walter Hübsch; Hilmar Bischoff, all of Wuppertal; Dieter Petzinna, Duesseldorf; Delf Schmidt, Wuppertal, all of Fed. Rep. of Germany; Günter Thomas, Arese, Italy

[73] Assignee: Bayer Aktiengesellschaft, Leverkusen, Fed. Rep. of Germany

[21] Appl. No.: 314,681

[22] Filed: Feb. 22, 1989

[30] Foreign Application Priority Data

Feb. 25, 1988 [DE] Fed. Rep. of Germany ....... 3805884
Nov. 24, 1988 [IT] Italy ................ 22722 A/88

[51] Int. Cl.$^5$ .................. A61K 31/415; C07D 233/30
[52] U.S. Cl. .................... 514/392; 548/317; 548/320; 548/321; 548/322
[58] Field of Search ............... 548/317, 322, 320, 321; 514/386, 392

[56] References Cited

U.S. PATENT DOCUMENTS

| | | | |
|---|---|---|---|
| 2,514,380 | 7/1950 | Duschinsky | 548/317 X |
| 2,602,798 | 7/1952 | Hoefle et al. | 548/322 |
| 3,021,338 | 2/1962 | Bortnick | 548/317 X |
| 3,184,460 | 5/1965 | Akkermann et al. | 548/317 X |
| 3,234,000 | 2/1966 | Bartels et al. | 548/317 X |
| 3,641,049 | 2/1972 | Sandstrom et al. | 548/322 |
| 3,728,355 | 4/1973 | D'Amico et al. | 548/322 X |
| 4,011,238 | 3/1977 | Fontanella et al. | 548/322 X |
| 4,188,397 | 2/1980 | Hill | 548/322 X |
| 4,315,022 | 2/1982 | Wootton et al. | 514/386 |

FOREIGN PATENT DOCUMENTS

| | | |
|---|---|---|
| 0022478 | 1/1981 | European Pat. Off. . |
| 0051829 | 5/1982 | European Pat. Off. . |
| 0104342 | 4/1984 | European Pat. Off. . |
| 0114027 | 7/1984 | European Pat. Off. . |
| 0130526 | 1/1985 | European Pat. Off. . |
| 3504677 | 8/1986 | Fed. Rep. of Germany . |
| 86/00307 | 6/1985 | PCT Int'l Appl. . |
| 86/07054 | 5/1986 | PCT Int'l Appl. . |

Primary Examiner—Mary C. Lee
Assistant Examiner—Catherine Scalzo
Attorney, Agent, or Firm—Sprung, Horn Kramer & Woods

[57] ABSTRACT

HMG-CoA reductase-inhibiting compounds of the formula

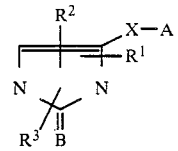

in which
R$^1$ is an optionally substituted alkyl as cycloalkyl radical,
R$^2$ is an optionally substituted aryl or heteroaryl radical,
R$^3$ is hydrogen or an organic radical,
B is O or S,
X is —CH$_2$—CH$_2$ or —CH=CH—,
A is

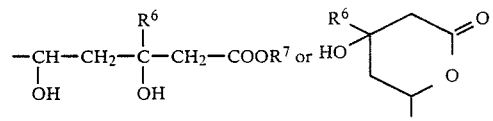

R$^6$ is hydrogen or alkyl, and
R$^7$ is hydrogen, alkyl, aralkyl, aryl or a cation.

11 Claims, No Drawings

SUBSTITUTED IMIDAZOLINONES AND IMIDAZOLINETHIONES

The invention relates to substituted imidazolinones and imidazolinethiones, intermediates for their preparation, their preparation and their use in medicaments.

It has been disclosed that lactone derivatives isolated from fungal cultures are inhibitors of 3-hydroxy-3-methyl-glutaryl coenzyme A reductase (HMG-CoA reductase) [mevinolin, EP No.22,478; U.S. Pat. No. 4,231,938]. Moreover, certain indole derivatives of pyrazole derivatives have also been disclosed as inhibitors of HMG-CoA reductase [EP-A No. 1,114,027; U.S. Pat. No. 4,613,610].

Substituted imidazolinones and imidazolinethiones of the general formula (I)

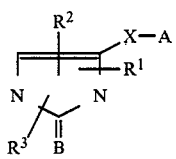

in which $R^1$ stands for cycloalkyl, or stands for alkyl which can b substituted by halogen, cyano, alkoxy, alkylthio, alkylsulphonyl, trifluoromethyl, trifluoromethoxy, trifluoromethylthio, trifluoromethylsulphonyl, alkoxycarbonyl or acyl, or by a group of the formula —$NR^4R^5$, wherein $R^4$ and $R^5$ are identical or different and denote alkyl, aryl, aralkyl, acyl, alkylsulphonyl or arylsulphonyl, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals of the last-mentioned substituents can be monosubstituted, disubstituted or trisubstituted by halogen, cyano, trifluoromethyl, trifluromethoxy, alkyl, alkoxy, alkylthio or alkylsulphony, each of which is identical or different, $R^2$ stands for heteroaryl which can be monosubstituted, disubstituted or trisubstituted by halogen, alkyl, alkoxy, alkylthio, alkylsulphonyl, aryl, aryloxy, arylthio, arylsulphonyl, trifluoromethyl, trifluoromethoxy, trifluoromethylthio or alkoxycarbonyl, or by a group of the formula —$NR^4R^5$, each of which is identical or different, wherein $R^4$ and $R^5$ have the abovementioned meaning, or $R^2$ stands for aryl which can be monosubstituted to pentasubstituted by alkyl, alkoxy, alkylthio, alkylsulphonyl, aryl, aryloxy arylthio, arylsulphonyl, aralkyl, aralkoxy aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl or dialkylcarbamoyl, or by a group of the formula —$NR^4R^5$, each of which is identical or different, wherein $R^4$ and $R^5$ have the abovementioned meaning, $R^3$ stands for hydrogen or for acyl, alkylsulphonyl or arylsulphonyl, where the aryl radical can be substituted by alkyl or halogen, or stands for aminocarbonyl, alkylaminocarbonyl, dialkylaminocarbonyl, arylaminocarbonyl or alkoxycarbonyl, or stands for cycloalkyl, or stands for alkyl which can be substituted by halogen, cyano, alkoxy, alkythio, alkylsulphonyl, trifluoromethyl, trifluoromethoxy, trifluoromethylthio, trifluoromethylsulphonyl, alkoxycarbonyl or acyl, or by a group of the formula —$NR^4R^5$, wherein $R^4$ and $R^5$ have the abovementioned meaning, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals of the lastmentioned substituents can be monosubstituted, disubstituted or trisubstituted by halogen, cyano, trifluoromethyl, trifluoromethoxy, alkyl, alkoxy, alkylthio or alkylsulphonyl, each of which is identical or different, or $R^3$ stands for heteroaryl which be monosubstituted, disubtituted or trisubstituted by halogen, alkyl, alkoxy, alkylthio, alkylsulphonyl aryl, aryloxy, arylthio, arylsulphonyl, trifluoromethyl, trifluoromethoxy, trifluoromethylthio or alkoxycarbonyl, or by a group of the formula —$NR^4R^5$, each of which is identical or different, wherein $R^4$ and $R^5$ have the abovementioned meaning, or $R^3$ stands for aryl which can be monosubstituted to pentasubstituted by alkyl, alkxoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl or dialkylcarbamoyl, or by a group of the formula —$NR^4R^5$, each of which is identical or different, wherein $R^4$ and $R^5$ have the abovementioned meaning, B stands for oxygen or sulphur, X stands for a group of the form —$CH_2$—$CH_2$— or —CH=CH—, and A stands for a group of the formula

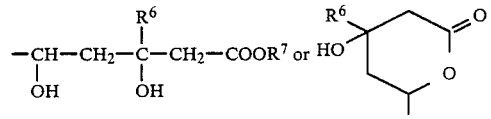

wherein $R^6$ denotes hydrogen or alkyl and $R^7$ denotes hydrogen, an alkyl, aralkyl or aryl radical or a cation, have been found.

Surprisingly, the substituted imidazolinones and imidazolinethiones according to the invention show considerable pharmacological action, in particular a good inhibitory action on HMG-CoA reductase(3-hydroxy-3-methylglutaryl coenzyme A reductase).

Cycloalkyl in general stands for a cyclic hydrocarbon radical having 3 to 8 carbon atoms. The cyclopropyl, cyclopentyl and cyclohexyl rings are preferred. Examples which may be mentioned are cyclopropyl, cyclopentyl, cyclohexyl, cycloheptyl and cyclooctyl.

Alkyl in general stands for a straight-chain or branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl an isooctyl.

Alkoxy in general stands for a straight-chain or branched hydrocarbon radical having 1 to 12 carbon atoms which is bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

Alkylthio in general stands for a straight-chain or branched hydrocarbon radical having 1to 12 carbon atoms which is bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio or isooctylthio.

Alkylsulphonyl in general stands for straight-chain or branched hydrocarbon radical having 1 to 12 carbon atoms which is bonded via an $SO_2$ group. Lower alkylsulphonyl having 1 to about 6 carbon atoms is preferred. Examples which may be mentioned are: methylsulphonyl, ethylsulphonyl, propylsulphonyl, isopropylsulphonyl, butylsulphonyl, isobutylsulphonyl, pentylsulphonyl, isopentylsulphonyl, hexylsulphonyl and isohexylacylsulphonyl, Aryl in general stands for an aromatic radical having 6 to about 12 carbon atoms. Preferred aryl radicals are phenyl, naphthyl and biphenyl.

Aryloxy in general stands for an aromatic radical having 6 to about 12 carbon atoms which is bonded via an oxygen atom. Preferred aryloxy radicals are phenoxy or naphthyloxy.

Arylthio in general stands for an aromatic radical having 6 to about 12 carbon atoms which is bonded via a sulphur atom. Preferred arylthio radicals are phenylthio or naphthylthio.

Arylsulphonyl in general stands for an aromatic radical having 6 to about 12 carbon atoms which is bonded via an $SO_2$ group. Examples which may be mentioned are: phenylsulphonyl, naphthylsulphonyl and biphenylsulphonyl.

Aralkyl in general stands for an aryl radical having 7 to 14 carbon atoms which is bonded via an alkylene chain. Aralkyl radicals having 1 to 6 carbon atoms in the aliphatic moiety and 6 to 12 carbon atoms in the aromatic moiety are preferred. Examples which may be mentioned are the following aralkyl radicals: benzyl, naphthylmethyl, phenethyl and phenylpropyl.

Aralkoxy in general stands for an aralkyl radical having 7 to 14 carbon atoms, the alkylene chain being bonded via an oxygen atom. Aralkoxy radicals having 1 to 6 carbon atoms in the aliphatic moiety 6 to 12 carbon atoms in the aromatic moiety are preferred. Examples which may be mentioned are the following aralkoxy radicals: benzyloxy, naphthylmethoxy, phenethoxy and phenylpropoxy.

Aralkylthio in general stands for an aralkyl radical having 7 to about 14 carbon atoms, the alkyl chain being bonded via a sulphur atom. Aralkylthio radicals having 1 to 6 carbon atoms in the aliphatic moiety and 6 to 12 carbon atoms in the aromatic moiety are preferred. Examples which may be mentioned are the following aralkylthio radicals: benzylthio, naphthylmethylthio, phenethylthio and phenylpropylthio.

Aralkylsulphonyl in general stands for an aralkyl radical having 7 to about 14 carbon atomss, the alkyl radical being bonded via an $SO_2$ link. Aralkylsulphonyl radicals having 1 to 6 carbon atoms in the aliphatic moiety and 6 to 12 carbon atoms in the aromatic moiety are preferred. Examples which may be mentioned are the following aralkylsulphonyl radicals: benzylsulphonyl, naphthylmethylsulphonyl, phenethylsulphonyl and phenylpropylsulphonyl.

Alkoxycarbonyl can be represented, for example, by the formula.

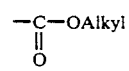

In this connection, alkyl stands for straight-chain or branched hydrocarbon radical having 1 to 12 carbon atoms. Lower alkoxycarbonyl having 1 to about 6 carbon atoms in the alkyl moiety is preferred. An alkoxycarbonyl having 1 to 4 carbon atoms in the alkyl moiety is particularly preferred. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

Acyl in general stands for phenyl or straight-chain or branched lower alkyl having 1 to 6 carbon atoms which are bonded via a carbonyl group. Phenyl and alkyl radicals having up to 4 carbon atoms are preferred. Examples which may be mentioned are: benzoyl, acetyl, ethylcarbonyl, propylcarbonyl, isopropylcarbonyl, butylcarbonyl and isobutylcarbonyl.

Halogen in general stands for fluorine, chlorine, bromine or iodine, preferably for fluorine, chlorine or bromine. Particularly preferably, halogen stands for fluorine or chlorine.

Heteroaryl in the scope of the abovementioned definition in general stands for a 5- to 6-membered aromatic ring which can contain oxygen, sulphur and/or nitrogen as hetero atoms and onto which can be fused further aromatic rings. 5- and 6-membered aromatic rings which contain one oxygen, one sulphur and/or up to 2 nitrogen atoms and which are optionally fused to benzene are preferred. Heteroaryl radicals which may be mentioned as particularly preferred are: thienyl, furyl, pyrolyl, pyrazolyl, pyridyl, pyrimidyl, pyrazinyl, pyridazinyl, quinolyl, isoquinolyl, quinazolyl, quinoxalyl, phthalazinyl, cinnolyl, thiazolyl, benzothiazolyl, isothiazolyl, oxazolyl, benzoxazolyl, isoxazolyl, imidazolyl, benzimidazolyl, pyrazolyl, indolyl and isoindolyl.

If $R^7$ stands for an alkyl, aryl or aralkyl radical, it forms an ester group.

Physiologically tolerable esters which are easily hydrolyzed in vivo to a free carboxyl group and a corresponding physiologically tolerable alcohol are preferred. These include, for example, alkyl esters ($C_1$ to $C_6$) and aralkyl esters ($C_7$ to $C_{10}$), preferable lower alkyl esters and benzyl esters. Methyl esters, ethyl esters, propyl esters and benzyl esters are particularly preferred.

If $R^7$ stands for a cation, then a physiologically tolerable metal cation or ammonium cation is preferably meant. In this connection, alkali metal cations or alkaline earth metal cations such as, for example sodium cations, potassium cations, magnesium cations or calcium cations, and also aluminum cations or ammonium cations, and also non-toxic substituted ammonium cations from amines such as dilower alkylamines, trilower alkylamines, dibenzylamine, N,N'-dibenzylethylenediamine, N-benzyl-β-phenylethylamine, N-methylmorpholine or N-ethylmorpholine, dihydroabiethylamine, N,N'-bis-dihydroabiethyletylenedimane, N-lower alkylpiperidine and other amines which can be used for the formation of salts are preferred.

In the context of the present invention, the substituted imidazolinones and imidazolinethiones preferably correspond to the general formula

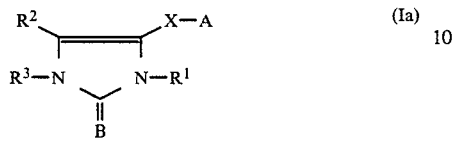

(Ia)

in which $R^1$, $R^2$, $R^3$, X, A and B have the abovementioned meaning, and to the general formula

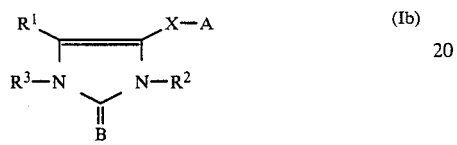

(Ib)

in which $R^1$, $R^2$, $R^3$, X, A and B have the abovementioned meaning.

Preferred imidazolinones and imidazolinethiones of the formula (I) are those in which $R^1$ stands for cyclopropyl, cyclopentyl or cyclohexyl, or stands for lower alkyl which be substituted by fluorine, chlorine, bromine cyano, lower alkoxy, lower alkylthio, lower alkylsulphonyl, trifluoromethyl, trifluorometho , trifluoromethylsulphonyl, lower alkoxycarbony benzoyl, lower alkylcarbonyl, by a group of the formula $-NR^4R^5$, wherein $R^4$ and $R^5$ are identical or different and denote lower alkyl, phenyl, benzyl, acetyl, benzoyl, phenylsulphonyl or lower alkylsulphonyl, or by pyridyl, pyrimidyl, pyrazinyl, pyridazinyl, quinolyl, isoquinolyl, pyrryl indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, where the heteroaryl and aryl radicals mentioned can be monosubstituted or disubstituted by fluorine, chlorine, bromine, lower alk lower alkoxy, trifluoromethyl, or trifluoromethoxy, each of which is identical or different, $R^2$ stands for thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl which can be monosubstituted or disubstituted by fluorine, chlorine, bromine, lower alkyl, lower alkoxy, phenyl, phenoxy, trifluoromethyl, trifluoromethoxy or lower alkoxy carbonyl, each of which is identical or different, or stands for phenyl or naphthyl which can be monosubstituted to tetrasubstitute by lower alkyl, lower alkoxy, lower alkylthio, lower alkylsulphony, phenyl, phenyloxy, phenylthio, phenylsulphonyl, benzyl, benzyloxy benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio or lower alkoxycarbonyl, or by a group of the formula $-NR^4R^5$, each of which is identical or different, where $R^4$ and $R^5$ have the abovementioned meaning, $R^3$ stands for hydrogen, or for benzoyl or lower alkylcarbonyl, or stands for lower alkylsulphonyl, phenylsulphonyl or tolylsulphonyl, or stands for aminocarbonyl, lower alkylaminocarbonyl, di-lower alkylaminocarbonyl, phenylaminocarbonyl or lower alkoxycarbonyl, or stands for cyclopropyl, cyclopentyl or cyclohexyl or stands for lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl, lower alkylcarbonyl, by a group of the formula $-NR^4R^5$, wherein $R^4$ and $R^5$ have the abovementioned meaning, or by pyridyl, pyrimidyl, pyrazinyl, pyridazinyl, quinolyl, isoquinolyl, pyrrolyl indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylio or phenylethylsulphonyl, where the heteroaryl and aryl radicals mentioned can be monosubstituted or disubstituted by fluorine, chlorine, bromine, lower alkyl, lower alkoxy trifluoromethyl or trifluoromethoxy, each of which is identical or different, $R^3$ stands for thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, beneoxazolyl or benzimidazolyl, each of which can be monosubstituted or disubstituted by fluorine, chlorine, bromine, lower alkyl, lower alkoxy, phenyl, phenoxy, trifluoromethyl, trifluoromethoxy, or lower alkoxycarbonyl, each of which is identical or different, or $R^3$ stands for phenyl or naphthyl which can be monosubstituted to tetrasubstituted by lower alkyl, lower alkoxy, lower alkylthio lower alkylsulphonyl, phenyl, phenyloxy, phenylthio, phenylsulphonyl, benzyl, benzyloxy, benzylthio, benzylsulphonyl, phenylethyl, phenylethoxy, phenylethylthio, phenylethylsulphonyl, fluorine, chlorine, bromine, cyano, trifluoromethyl, trifluoromethoxy, trifluoromethylthio or lower alkoxycarbonyl, or by a group of the formula $-NR^4R^5$, of which is identical or different, where $R^4$ and $R^5$ have the abovementioned meaning, B stands for O or S, X stands for a group of the formula $-CH_2-CH_2-$ or $-CH=CH-$, A stands for a group of the formula

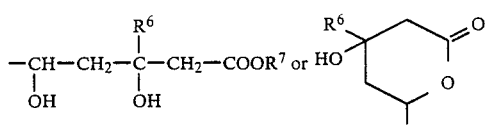

wherein
$R^6$ denotes hydrogen or lower alkyl, and $R^7$ denotes alkyl ($C_1$ to $C_6$), ($C_6$ to $C_{12}$) or aralkyl ($C_7$ to $C_{10}$), or denotes a physiologically tolerable cation.

Particularly preferred compounds of the general formula (I) are those in which $R^1$ stands for cyclopropyl, cyclopentyl or cyclohexyl, or stands for methyl, ethyl, propyl, isopropyl, butyl, sec.-butyl or tert.butyl, each of which can be substituted by fluorine, chlorine, bromine, cyano, methoxy, ethoxy, propoxy, isopropoxy, butoxy, sec.butoxy, tert.butoxy, methylthio, ethylthio, propylthio, isopropylthio, methylsulphonyl, ethylsulphonyl, propylsulphonyl, isopropylsulphonyl, trifluoromethyl, trifluoromethoxy, methoxycarbonyl, ethoxycarbonyl, butoxycarbonyl, isobutoxycarbonyl, tert.-butoxycarbonyl, benzoly, acetyl, pyridyl, pyrimidyl, thienyl, furyl, phenyl, phenoxy, phenylthio, phenylsulphonyl, benzyloxy, benzylthio or benzylsulphonyl, $R^2$ stands for pyridyl, pyrimidyl, quinolyl or isoquinolyl which can be substituted by fluorine, chlorine, methyl, methoxy or trifluoromethyl, or stands for phenyl which can be monosubstituted, disubstituted or trisubstituted by methyl, ethyl, propyl, isopropyl, butyl, isobutyl, tert.-butyl, methoxy, ethoxy, propoxy, isopropoxy, butoxy, isobutoxy, tert.butoxy, methylthio, ethylthio, propylthio, isopropylthio, methylsulphonyl, ethylsulphonyl, propylsulphonyl, isopropylsulphonyl, phenyl, phenoxy, benzyl, benzyloxy, fluorine, chlorine, bromine, cyano, trifluoromethyl, trifluoromethoxy, methoxycarbony ethoxycarbonyl, propoxycarbonyl, isopropoxycarbonyl, butoxycarbonyl, isobutoxycarbonyl or tert.butoxycarbonyl, each of which is identical or different, $R^3$ stands for hydrogen, cyclopropyl, cyclopentyl or cyclohexyl, or stands for methyl, ethyl, propyl, isopropyl, butyl, isobutyl, tert.butyl, pentyl, isopentyl, hexyl or isohexyl which can be substituted by fluorine, chlorine, bromine, cyano, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, trifluoromethyl, trifluoromethoxy, methoxycarbonyl, ethoxycarbonyl, propoxycarbonyl, isopropoxycarbonyl, butoxycarbonyl, isobutoxycarbonyl, tert.butoxycarbonyl, benzoyl, acetyl or ethylcarbonyl, or by a group $—NR^4R^5$, where $R^4$ and $R^5$ are identical or different and denote methyl, ethyl, propy isopropyl, butyl, isobutyl, tert.butyl, phenyl, benzyl, acetyl, methylsulphonyl, ethylsulphonyl, propylsulphonyl, isopropylsulphonyl or phenylsulphonyl, or by pyridyl, pyrimidyl, pyrazinyl, pyridazinyl, quinoline, isoquinolyl, thienyl, furyl, phenyl, phenoxy, phenylthio, phenylsulphonyl, benzyloxy, benzylthio or benzylsulphonyl, where the heteroaryl and aryl radicals mentioned can be substituted by fluorine, chlorine, methyl, ethyl, propyl, isopropyl, isobutyl, tert.butyl, methoxy, ethoxy, propoxy, isopropoxy, butoxy, isobutoxy, tert.butoxy, trifluoromethyl or trifluoromethoxy, or $R^3$ stands for thienyl, furyl, pyridyl, pyrimidyl, pyrazinyl, pyridazinyl, oxazolyl, isooxazolyl, imidazolyl, pyrazolyl, thiazolyl, isothiazolyl, quinolyl, isoquinolyl, benzoxazolyl, benzimidaquinolyl, zolyl or benzthiazolyl, where the radicals mentioned can be substituted by fluorine, chlorine, methyl, ethyl, propyl, isopropyl, butyl, isobutyl, tert.butyl, methoxy, ethoxy, propoxy, isopropoxy, butoxy, isobutoxy, tert.butoxy, phenyl, phenoxy, trifluoromethyl, trifluoromethoxy, methoxycarbonyl, ethoxycarbonyl, isopropoxycarbonyl, propoxycarbonyl, butoxycarbonyl, isobutoxycarbonyl or tert.butoxycarbonyl, or $R^3$stands for phenyl which can be monosubstituted, disubstituted or trisubstituted methyl, ethyl, propyl, isopropyl, butyl, isobutyl, tert.butyl, pentyl, isopentyl, hexyl, isohexyl, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsuphonyl, phenyl, phenoxy, phenylthio, phenylsulphonyl, benzyl, benzyloxy, benzylthio, benzylsulphonyl, fluorine, chlorine, bromine, cyano, trifluoromethyl, trifluoromethoxy, trifluoromethylthio, methoxycarbonyl, ethoxycarbonyl, propoxycarbonyl, isopropoxycarbonyl, butoxycarbony, isobutoxycarbonyl or tert.butoxycarbonyl, or by a group $—NR^4R^5$, each of which is identical or different, where $R^4$ and $R^5$ have the abovementioned meaning, or $R^3$ stands for benzoyl, acetyl, ethylcarbonyl, propylcarbonyl, isopropylcarbonyl, methylsulphonyl, ethylsulphonyl, propylsulphonyl isopropylsulphonyl, butylsulphonyl, isobutylsulphonyl, tert.butylsulylsulphonyl, phenylsulphonyl or tolylsulphonyl, stands for aminocarbonyl, methyl-, ethyl-, propyl-, isopropyl-, butyl-, isobutyl- or tert.butylaminocarbonyl, dimethyl-, diethyl-, dipropyl-, diisopropyl-, dibutyl- or diisobutylaminocarbonyl, phenylaminocarbonyl, methoxycarbonyl, ethoxycarbonyl, propoxycarbonyl, isopropoxycarbonyl, butoxycarbonyl, isobutoxycarbonyl or tert.butoxycarbonyl, B stands for oxygen or sulphur, X stands for a group of the formula $—CH_2—CH_2—$ or $—CH=CH—$, A stands for a group of the formula

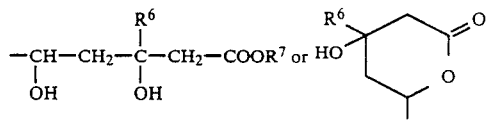

wherein $R^6$ denotes hydrogen, methyl, ethyl, propyl, isopropyl, butyl, isobutyl or tert.butyl, and $R^7$ denotes hydrogen, methyl, ethyl, propyl, isopropyl, butyl, isobutyl tert.butyl or benzyl, or denotes a sodium potassium, calcium, magnesium or ammonium cation.

The substituted imidazo and imidazolinethiones of the general formula (I) according to the invention have several asymmetric carbon atoms and can therefore exist in various stereochemical forms. The invention relates both to the individual isomers and to their mixtures.

Depending on the meaning of the group X or the radical A, different stereoisomers result which are illustrated in more detail in the following: (a) If the group $—X—$ stands for a group of the formula $—CH=CH—$, then the compounds a rding to the invention can exist in two stereoisomeric forms which can have the E configuration (II) or Z configuration (III) on the double bond:

(E configuration)

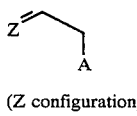

(Z configuration)

where Z stands for the radical

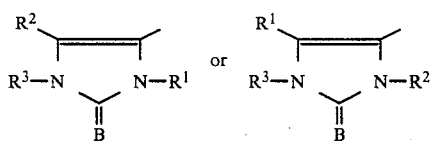

Those compounds of the general formula (I) which have the E configuration (II) are preferred.

(b) If the radical —A— stands for a group of the formula

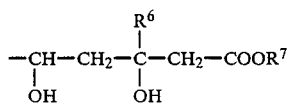

then the compounds of the general formula (I) possess at least two asymmetric carbon atoms, namely the two carbon atoms to which the hydroxyl groups are bonded. Depending on the relative position of these hydroxyl groups to one another, the compounds according to the invention can be present in the erythro configuration (IV) or in the three configuration (V).

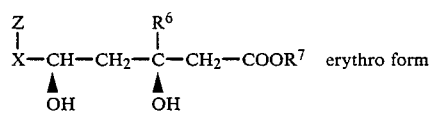

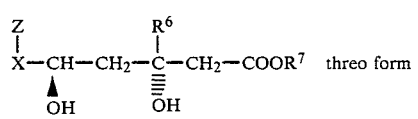

Two enantiomers again exist in each case both of the compounds in the erythro and the three configuration, namely the 3R,5S isomer or 3S,5R isomer (erythro form) and 3R,5R-isomer and 3S,5S-isomer (three form).

In this connection, the isomers having the erythro configuration are preferred, the 3R,5S isomer and the 3R,5S-3S,5R-racemate being particularly preferred.

(c) If the radical —A— stands for a group of the formula

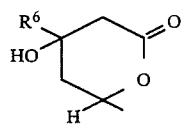

then the substituted imidazolinones and imidazolinethiones possess at least two asymmetric carbon atoms, namely the carbon atom to which the hydroxyl group is bonded, and the carbon atom to which the radical of the formula

Z—X— is bonded.

Depending on the position of the hydroxyl group to the free valency on the lactone ring, the substituted imidazolinones and imidazolinethiones can be present as cis-lactones (VI) or as trans-lactones (VII):

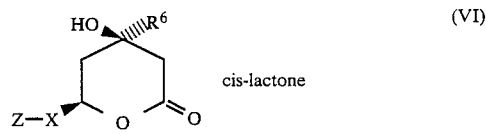

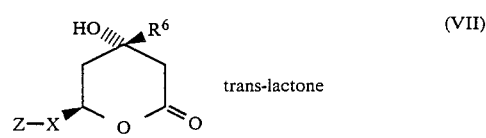

Two isomers again exist both of the cis-lactone and the trans-lactone, namely the 4R,6R-isomer or the 4S,6S-isomer (cis-lactone), and the 4R,6S-isomer or 4S,6R-isomer (trans-lactone). The trans-lactones are preferred isomers.

In this connection, the 4R,6S-isomer (trans) and the 4R,6S-4S,6R-racemates are preferred.

For example, the following isomeric forms of the substituted imidazolinones and imidazolinethiones may be mentioned:

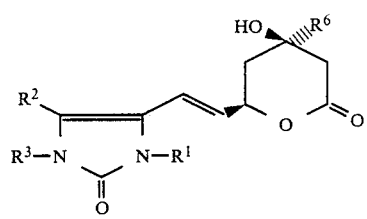

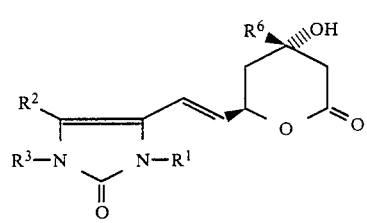

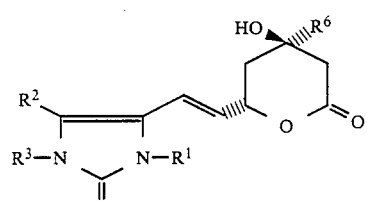

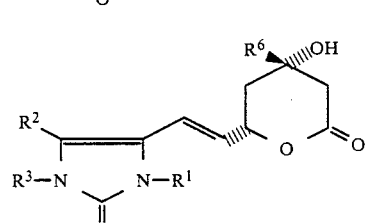

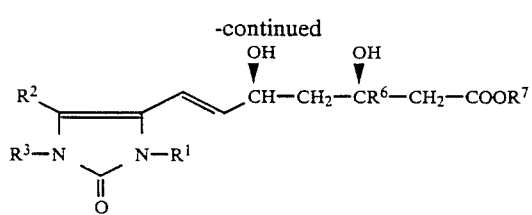
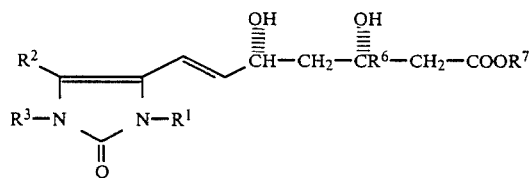
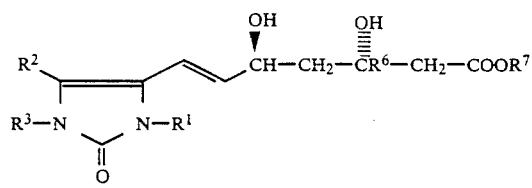
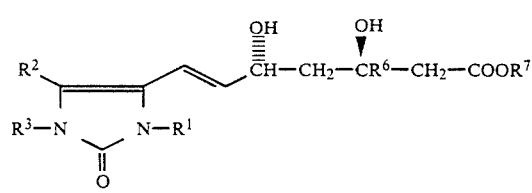
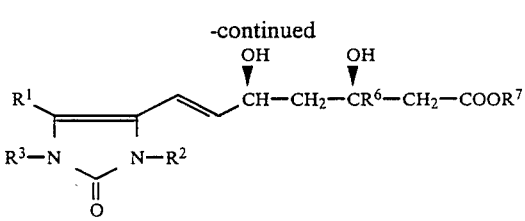
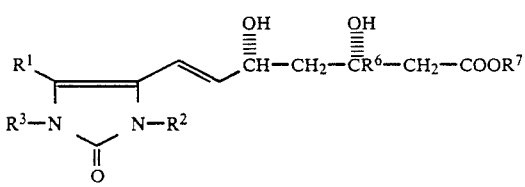
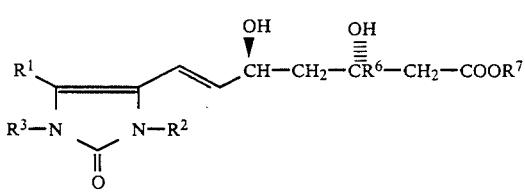
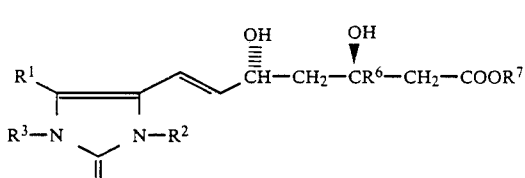
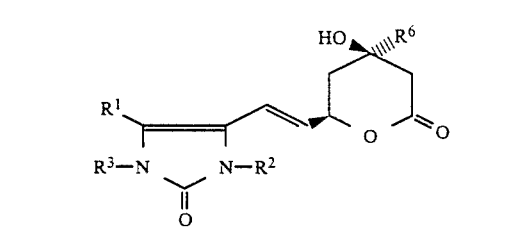

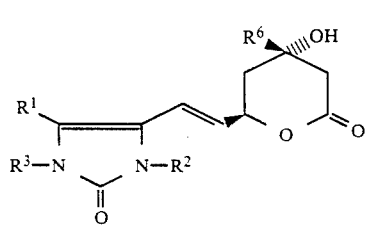

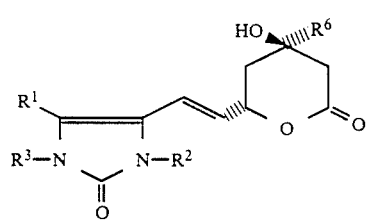

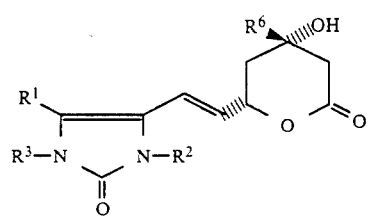

Very particularly preferred compounds of the general formula (Ia) and (Ib) are those in which $R^1$ stands for cyclopropyl, methyl, ethyl, propyl, isopropyl, butyl, isobutyl or tert.-butyl.

$R^2$ stands for phenyl which can be monosubstituted or disubstituted by methyl and/or trifluoromethyl, $R^3$ stands for methyl, isopropyl, tert.-butyl or stands for phenyl which can be monosubstituted or disubstituted by methyl, methoxy, fluorine and/or chlorine, B stands for oxygen or sulphur, X stands for a group of the formula

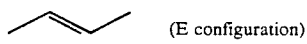 (E configuration)

and

A stands for a group of the formula

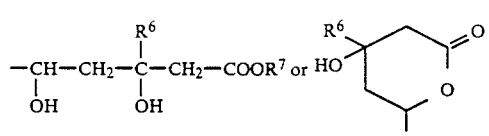

wherein $R^6$ denotes hydrogen and $R^7$ denotes hydrogen, methyl or ethyl or denotes a sodium or potassium cation.

In addition, a process for the preparation of the substituted imidazolinones and imidazolinethiones of the general formula (I)

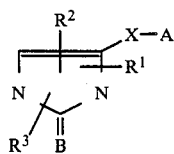
(I)

in which
R¹, R², R³, A, B and X have the abovementioned meaning, has been found, which is characterized in that ketones of the general formula (VIII)

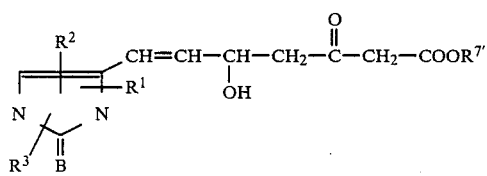
(VIII)

in which
R¹, R², R³ and B have the abovementioned meaning, and
R⁷' stands for alkyl ($C_1$ to $C_6$), aryl ($C_6$ to $C_{12}$) or aralkyl ($C_7$ to $C_{10}$),
are reduced,
in the case of the preparation of the acids the esters are hydrolyzed,
in the case of the preparation of the lactones the carboxylic acids are cyclized,
in the case of the preparation of the salts either the esters or the lactones are hydrolyzed,
in the case of the preparation of the ethylene compounds (X=—$CH_2$—$CH_2$—), the ethene compounds (X=—CH=CH—) are hydrogenated by customary methods, and, if appropriate, isomers are resolved.

The process according to the invention can be illustrated by the following reaction scheme:

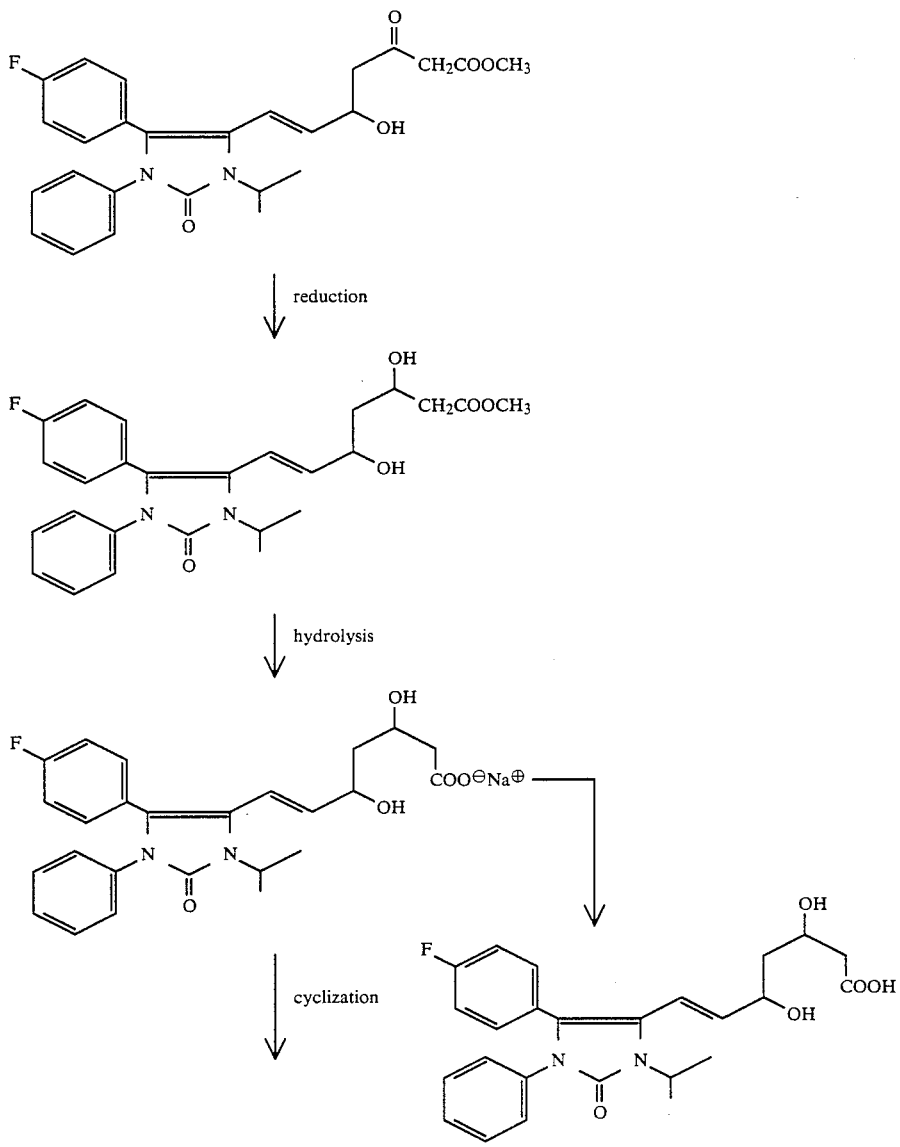

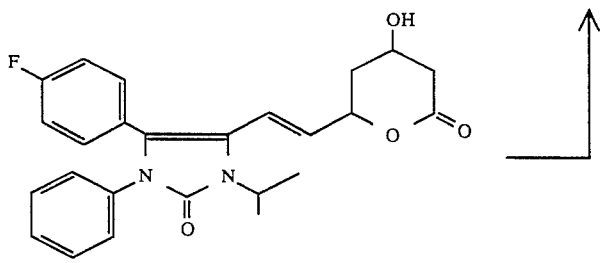

The reduction can be carried out using the customary reducing agents, preferably using those which are suitable for the reduction of ketones to hydroxy compounds. In this connection, reduction using metal hydrides or complex metal hydrides in inert solvents, if desired in the presence of a trialkylborane, is particularly suitable. Reduction is preferably carried out using complex metal hydrides such as, for example, lithium borohydride, sodium borohydride, potassium borohydride, zinc borohydride, lithium trialkylborohydrides, sodium trialkylborohydrides, sodium cyanoborohydride or lithium aluminium hydride. Reduction is very particularly preferably carried out using sodium borohydride in the presence of triethylborane.

Suitable solvents in this connection are the customary organic solvents which do not change under the reaction conditions. These preferably include ethers such as, for example, diethyl ether, dioxane, tetrahydrofuran or dimethoxyethane, or halogenated hydrocarbons such as, for example, dichloromethane, trichloromethane, tetrachloromethane, 1,2-dichloroethane, or hydrocarbons such as, for example, benzene, toluene or xylene. It is also possible to employ mixtures of the solvents mentioned.

Reduction of the ketone group to the hydroxyl group is particularly preferably carried out under conditions in which the other functional groups such as, for example, the alkoxycarbonyl groups are not changed. The use of sodium borohydride as a reducing agent in the presence of triethylborane in inert solvents such as, preferably, ethers is particularly suitable for this.

Reduction is in general carried out in a temperature range from −80° C. to room temperature (30° C.), preferably from −78° C. to 0° C.

The process according to the invention is in general carried out at atmospheric pressure. However, it is also possible to carry out the process at underpressure or at overpressure (for example in a range from 0.5 to 5 bar).

In general, the reducing agent is used in an amount from 1 to 2 moles, preferably from 1 to 1.5 moles, relative to 1 mole of the keto compound.

Under the abovementioned reaction conditions, the carbonyl group is in general reduced to the hydroxyl group without reduction of the double bond to the single bond taking place.

To prepare compounds of the general formula (I), in which X stands for an ethylene grouping, the reduction of the ketones (III) can be carried out under those conditions under which both the carbonyl group and the double bond are reduced.

Moreover, it is also possible to carry out the reduction of the carbonyl group and the reduction of the double bond in two separate steps.

The carboxylic acids in the context of the general formula (I) correspond to the formula (Ic)

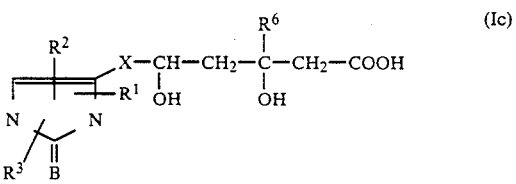

in which $R^1$, $R^2$, $R^3$, $R^6$, B and X have the abovementioned meaning.

The carboxylic acid esters in the context of the general formula (I) correspond to the formula (Id)

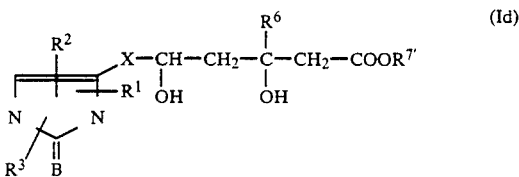

in which
$R^1$, $R^2$, $R^3$, $R^6$, B and X have the abovementioned meaning, and
$R^{7'}$ stands for alkyl, arylkyl or aryl.

The salts of the compounds according to the invention in the context of the general formula (I) correspond to the formula (Ie)

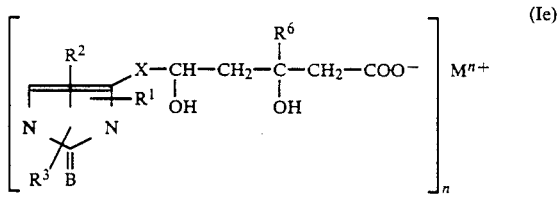

in which
$R^1$, $R^2$, $R^3$, $R^6$, B and X have the abovementioned meaning, and
$M^{n+}$ stands for an n-valent cation, wherein n denotes 1 or 2.

The lactones in the context of the general formula (I) correspond to the formula (If)

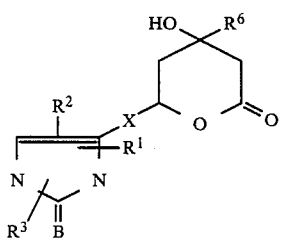

(If)

in which $R^1$, $R^2$, $R^3$, $R^6$, B and X have the abovementioned meaning.

To prepare the carboxylic acids of the general formula (Ic) according to the invention, the carboxylic acid esters of the general formula (Id) or the lactones of the general formula (If) are in general hydrolyzed by customary methods. Hydrolysis is in general carried out by treating the esters or the lactones with customary bases in inert solvents, where the salts of the general formula (Ie) in general first result, which can subsequently be converted into the free acids of the general formula (Ic) by treating with acid in a second step.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert.butoxide. Sodium hydroxide or potassium hydroxide are particularly preferably employed.

Suitable solvents for the hydrolysis are water or the organic solvents which are customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from 0° C. to +100° C., preferably from +20° C. to +80° C.

In general, the hydrolysis is carried out at atmospheric pressure. However, it is also possible to work at underpressure or at overpressure (for example from 0.5 to 5 bar).

In carrying out the hydrolysis, the base is in general employed in an amount from 1 to 3 moles, preferably from 1 to 1.5 moles, relative to 1 mole of the ester or the lactone. Molar amounts of the reactants are particularly preferably used.

In carrying out the reaction, the salts of the compounds (Ie) according to the invention result in the first step as intermediates which can be isolated. The acids (Ic) according to the invention are obtained by treating the salts (Ie) with customary inorganic acids. These preferably include mineral acids such as, for example, hydrochloric acid, hydrobromic acid, sulphuric acid or phosphoric acid. In this connection, it has proved advantageous in the preparation of the carboxylic acids (Ic) to acidify the basic reaction mixture from the hydrolysis in a second step without isolation of the salts. The acids can then be isolated in a customary manner.

To prepare the lactones of the formula (If) according to the invention, the carboxylic acids (Ic) according to the invention are in general cyclized by customary methods, for example by heating the corresponding acids in inert organic solvents, if desired in the presence of molecular sieve.

Suitable solvents in this connection are hydrocarbons such as benzene, toluene, xylene, mineral oil fractions, or tetralin or diglyme or triglyme. Benzene, toluene or xylene are preferably employed. It is also possible to employ mixtures of these solvents mentioned. Hydrocarbons, in particular toluene, in the presence of molecular sieve are particularly preferably used.

The cyclization is in general carried out in a temperature range from −40° C. to +200° C., preferably from −25° C. to +50° C.

The cyclization is in general carried out at atmospheric pressure, but it is also possible to carry out the process at underpressure or at overpressure (for example in a range from 0.5 to 5 bar).

Moreover, the cyclization is also carried out in inert organic solvents with the aid of cyclizing or dehydrating agents. Carbodiimides are preferably used as dehydrating agents in this connection. N,N'-dicyclohexylcarbodiimide paratoluenesulphonate, N,cyclohexyl-N'-[2-(N''-methylmorpholinium)ethyl]carbodiimide or N-(3-dimethylaminopropyl)-N'-ethylcarbodiimidehydrochloride are preferably employed as carbodiimides.

Suitable solvents in this connection are the customary organic solvents. These preferably include ethers such as diethyl ether, tetrahydrofuran or dioxane, or halogenated hydrocarbons such as methylene chloride, chloroform or carbon tetrachloride, or hydrocarbons such as benzene, toluene, xylene or mineral oil fractions. Chlorinated hydrocarbons such as, for example, methylene chloride, chloroform or carbon tetrachloride, or hydrocarbons such as benzene, toluene or xylene, or mineral oil fractions are particularly preferred. Chlorinated hydrocarbons such as, for example, methylene chloride, chloroform or carbon tetrachloride are particularly preferably employed.

The reaction is in general carried out in a temperature range from 0° C. to +80° C., preferably from +10° C. to +50° C.

In carrying out the cyclization, it has proved advantageous to employ the cyclization method with the aid of carbodiimides as dehydrating agents.

The resolution of the isomers into the individual stereoisomeric constituents is in general carried out by customary methods such as are described, for example, by E. L. Eliel, Stereochemistry of carbon compounds, McGraw Hill, 1962. In this connection, resolution of the isomers from the racemic lactone step is preferred. In this connection, the racemic mixture of the trans-lactone (VII) is particularly preferably converted by treating either with D-(+)-or L-(−)-α-methylbenzylamine by customary methods into the diastereomeric dihydroxy amides (Ig)

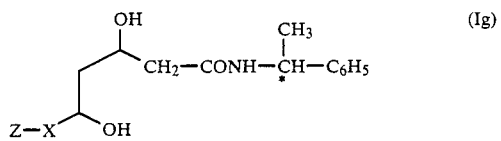

where Z and X have the abovementioned meaning, which can subsequently be resolved into the individual diastereomers by chromatography or crystallization as customary. Subsequent hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, yield the corresponding pure enantiomeric dihydroxy acids (Ic) which can be converted into the pure enantiomeric lactones by cyclization as described above. In general, it applies to the preparation of the compounds of the general formula (I) according to the invention in pure enantiomeric form that the configuration of the final product according to the method described above is dependent on the configuration of the starting material.

The resolution of isomers is illustrated by way of example in the following scheme:

A process has been found for the preparation of the ketones of the general formula (VIII) according to the invention

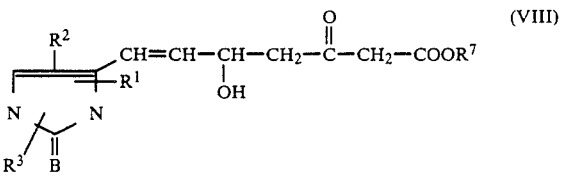

in which $R^1$, $R^2$, $R^5$ and $R^7$ have the abovementioned meaning, which is characterized in that aldehydes of the general formula (IX)

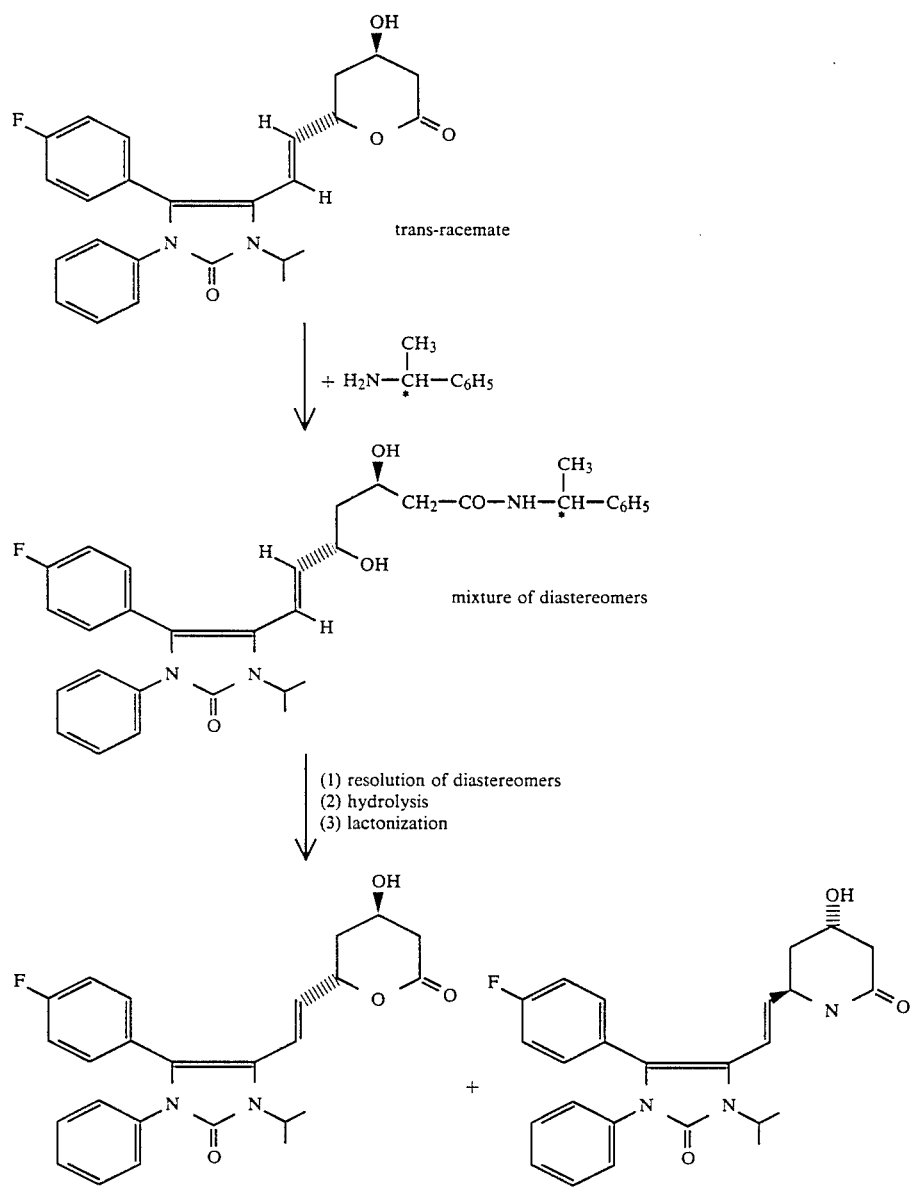

The ketones (VIII) employed as starting materials are new.

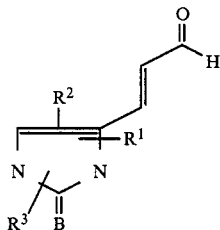

(IX)

in which $R^1$, $R^2$, $R^3$ and B have the abovementioned meaning, are reacted in inert solvents with acetoacetates of the general formula (X)

(X)

in which $R^{7'}$ has the abovementioned meaning, in the presence of bases.

The process according to the invention can be illustrated, for example, by the following reaction scheme:

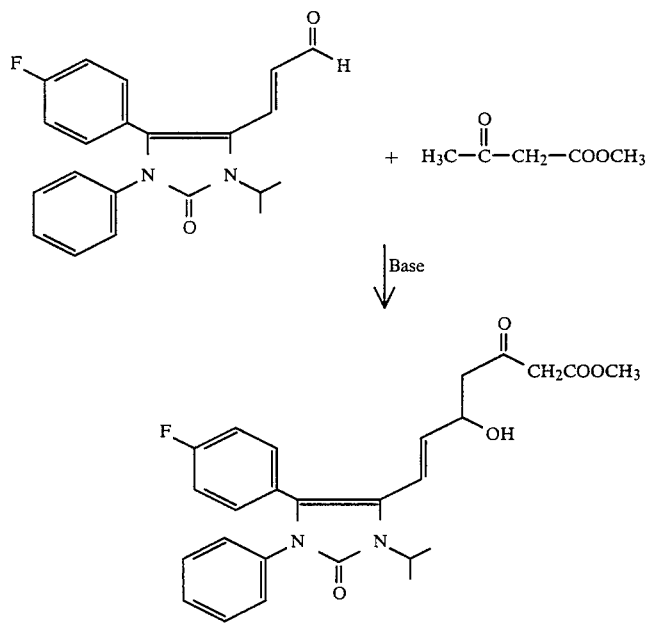

Suitable bases in this connection are the customary strong basic compounds. These preferably include organolithium compounds such as, for example, N-butyllithium, sec.butyllithium, tert.butyllithium or phenyllithium, or amides such as, for example, lithium diisopropylamide, sodium amide or potassium amide, or lithium hexamethyldisilylamide, or alkali metal hydrides such as sodium hydride or potassium hydride. It is also possible to employ mixtures of these bases mentioned. N-butyllithium or sodium hydride or their mixture are particularly preferably employed.

Additions of metal halides such as, for example, magnesium chloride or zinc bromide are advantageous in certain cases. The addition of zinc bromide is particularly preferred.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is also possible to employ mixtures of the solvents mentioned. Ethers such as diethyl ether or tetrahydrofuran are particularly preferably used.

The reaction is in general carried out in a temperature range from $-80°$ C. to $+50°$ C., preferably from $-20°$ C. to room temperature.

The process is in general carried out at atmospheric pressure, but it is also possible to work at underpressure or at overpressure, for example in a range from 0.5 to 5 bar.

In carrying out the process, the acetoacetate is in general employed in an amount from 1 to 2, preferably from 1 to 1.5, moles relative to 1 mole of the aldehyde.

The acetoacetates of the formula (X) employed as starting materials are known or can be prepared by known methods [Beilstein's Handbuch der organischen Chemie (Beilstein's Handbook of organic chemistry) III, 632; 438].

Acetoacetates which may be mentioned for the process according to the invention are, for example: methyl acetoacetate, ethyl acetoacetate, propyl acetoacetate and isopropyl acetoacetate.

The aldehydes of the general formula (IX) employed as starting materials are new.

In addition, a process has been found for the preparation of the aldehydes of the general formula (IX)

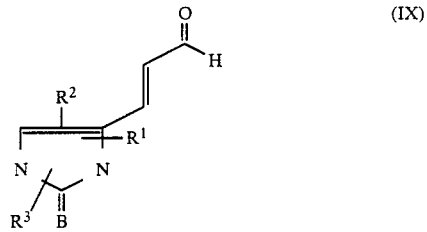

(IX)

in which R¹, R², R³ and B have the abovementioned meaning, which is characterized in that imidazolinones and imidazoline thiones of the general formula (XI)

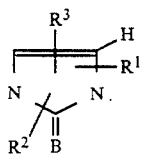

in which R¹, R², R³ and B have the abovementioned meaning, are reacted in inert solvents in the presence of auxiliaries with N,N-dialkylaminoacrolein of the formula (XII)

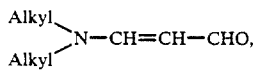

where alkyl stands for a straight-chain or branched hydrocarbon radical having 1 to 6 carbon atoms.

The process according to the invention can be illustrated, for example, by the following reaction scheme:

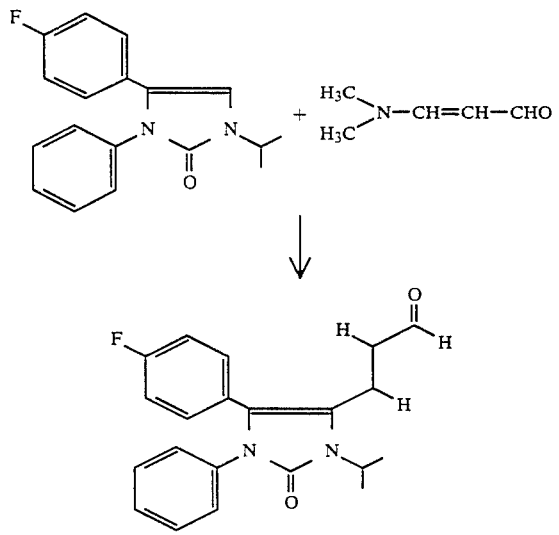

Suitable solvents in this connection are the customary organic solvents which are stable under the reaction conditions. These preferably include hydrocarbons such as benzene, toluene, xylene, hexane, mineral oil fractions, chlorobenzene or dichlorobenzene, or ethers such as diethyl ether, dioxane or tetrahydrofuran, or chlorinated hydrocarbons such as methylene chloride, chloroform or carbon tetrachloride or acetonitrile. It is also possible to employ mixtures of the solvents mentioned. Anhydrous acetonitrile or chloroform is particularly preferably used.

Acid chlorides are in general used as auxiliaries. Phosphorus oxychloride or phosgene, particularly preferably phosphorus oxychloride, is preferably employed.

The reaction is in general carried out in a temperature range from −20° C. to +150° C., preferably from 0° C. to +100° C.

The process is in general carried out at atmospheric pressure. However, it is also possible to carry out the process at underpressure or at overpressure (for example in a range from 0.5 to 5 bar).

In carrying out the process, the dimethylaminoacrolein is in general employed in an amount from 2 to 6, preferably from 3 to 4, moles relative to 1 mole of the pyrrole.

The imidazolinones and imidazolinethiones of the general formula (XI) employed as starting materials are known or can be prepared by known methods starting from aminoketones [EP-A-No. 222,664].

The aminoketones employed as starting materials are known or can be prepared by known methods [Methoden der organischen Chemie (Methods of organic chemistry), Vol. 7/2c, 2251 ff (1977); J. Org. Chem. 33, 494 (1968)].

The compounds of the general formula (I) possess useful pharmacological properties and can be employed in medicaments. In particular, they are inhibitors of 3-hydroxy-3-methyl-glutarylcoenzyme A (HMG-CoA) reductase and, as a result of this, inhibitors of cholesterolbiosynthesis. They can therefore be used for the treatment of (hyper)lipoproteinaemia, lipoproteinaemia or arteriosclerosis.

The new active compounds can be converted in a known manner into the customary formulations, such as tablets, dragees, pills, granules, aerosols, syrups, emulsions, suspensions and solutions, using inert, nontoxic, pharmaceutically suitable excipients or solvents. In this connection, the therapeutically active compound should in each case be present in a concentration of about 0.5 to 98% by weight, preferably 1 to 90% by weight, of the total mixture, i.e. in amounts which are sufficient in order to achieve the dosage range indicated.

The formulations are prepared, for example, by extending the active compound using solvents and/or excipients, if appropriate using emulsifiers and/or dispersants, where, for example, in the case of the use of water as a diluent, organic solvents can be used as auxiliary solvents if desired.

Auxiliaries which may be mentioned for example are: water, non-toxic organic solvents such as paraffins (for example mineral oil fractions), vegetable oils (for example groundnut/sesame oil), alcohols (for example: ethyl alcohol, glycerol), excipients, such as, for example, ground natural minerals (for example kaolins, argillaceous earths, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin- sulphite waste liquors, methylcellulose, starch and polyvinylpyrrolidone) and lubricants (for example magnesium stearate, talc, stearic acid and sodium lauryl sulphate).

Administration takes place in a customary manner, preferably orally, parenterally, perlingually or intravenously. In the case of oral administration, tablets can of course also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc can additionally be used for tabletting. In the case of aqueous suspensions, various flavor improvers or colorants can be added to the active compounds in addition to the abovementioned auxiliaries.

In the case of parenteral administration, solutions of the active compounds using suitable liquid excipients can be employed.

In general, it has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this it may be necessary to deviate from the amounts mentioned, depending on the body weight or the type of administration route, on individual behaviour towards the medicament, the manner of its formulation and the point in time or interval at which administration takes place. Thus in some cases it may be necessary to manage with less than the previously mentioned minimum amount, whereas in other cases the upper limit mentioned must be exceeded. In the case of the administration of larger amounts, it may be advisable to divide these into a number of individual doses over the day.

EXAMPLE 1

2-(Benzyl-methylamino)-1-(4-fluorophenyl)-1-oxo-ethane hydrochloride

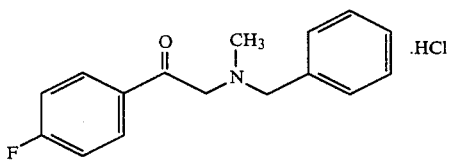

A solution of α-bromo-4-fluoroacetophenone (70.9 g, 0.33 mol) in 310 ml of diethyl ether is added dropwise at 0° C. to a solution of 81.8 g (0.68 mol) of N-methylbenzylamine in 220 ml of diethyl ether and the mixture is stirred overnight. The precipitate is separated off, hydrochloric acid gas is added to the filtrate, residual methylbenzylamine hydrochloride is separated off and the filtrate is stirred with acetone, the product being precipitated out.

Yield: 52.8 g 55% of theory $^1$H-NMR (DMSO): δ=2.85 (s, 3H, CH$_3$); 4.5 (br, 2H, CH$_2$); 5.1 (br, 2H, CH$_2$C=O); 7.3–8.2 (m, 9H, aromatic-H) ppm.

EXAMPLE 2

1-(4-Fluorophenyl)-2-methylamino-1-oxo-ethane hydrochloride

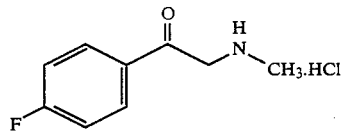

1.2 g of 10% palladium on charcoal is added under a nitrogen atmosphere to a solution of 10 g (31 mmol) of the compound from Example 1 in 200 ml of glacial acetic acid. After hydrogenation in a shaking apparatus (hydrogen uptake about 700 ml), the catalyst is filtered off, the solvent is removed by distillation and the product is washed with water and dried.

Yield: 7.2 g 97% of theory $^1$H-NMR (DMSO): δ=2.6 (s, 3H, CH$_3$); 4.75 (s, 2H, CH$_2$); 7.3–8.2 (m, 4H, aromatic-H); 9.5 (br, 2H, NH) ppm.

EXAMPLE 3

N-[2-(4-Fluorophenyl)-2-oxo-ethyl]-N-methyl-N'-phenylurea

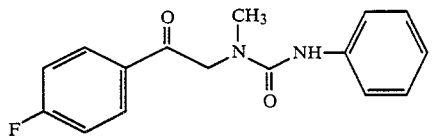

1.26 g (12.5 mmol) of phenyl isocyanate are used to a suspension of 3 g (12.5 mmol) of the compound from Example 2 in 30 ml of toluene and 1.5 g (12.5 mmol) of triethylamine are slowly added dropwise at 0° C. The mixture is stirred overnight at 25° C. The toluene phase is washed with water, the product precipitating out. After drying 3.54 g are obtained.

Yield: 98.9% of theory $^1$H-NMR (DMSO): δ=2.8 (s, 2H, CH$_2$); 3.35 (s, 3H, CH$_3$); 3.6 (s, 1H, NH); 6.9–7.6 (m, 9H, aromatic-H) ppm.

EXAMPLE 4

4-(4-Fluorophenyl)-1-methyl-3-phenyl-4-imidazolin-2-one

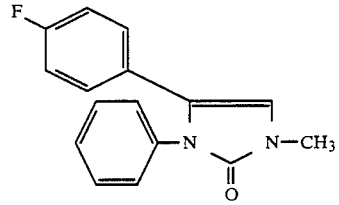

3.5 g (12.2 mmol) of the compound from Example 3 are heated under reflux for 24 hours in 50 ml of glacial acetic acid, the solvent is removed and the residue is washed with water. After drying 3.12 g are obtained.

Yield: 95.3% of theory $^1$H-NMR (DMSO): δ=3.3 (s, 3H, CH$_3$); 6.9 (s, 1H, imidazole-H); 7.0–7.5 (m, 9H, aromatic-H) ppm.

EXAMPLE 5

(E)-3-[4-(4-Fluorophenyl)-1-methyl-3-phenyl-4-imidazolin-2-on-5-yl]-prop-2-enal

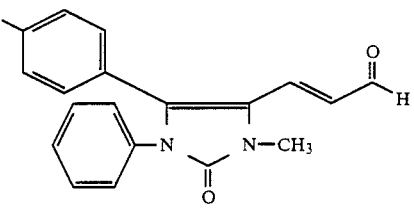

1.54 ml (14 mmol) of N,N-dimethylaminoacrolein in 5.3 ml of acetonitrile are added dropwise at 0°–5° C. in the course of 10 minutes under a nitrogen atmosphere to 1.37 ml (15 mmol) of phosphorus oxychloride in 8.5 ml of acetonitrile. After 10 minutes, a solution of 1.3 g (5 mmol) of the compound from Example 4 in 10 ml of acetonitrile is added and the mixture is heated overnight to boiling. 3.7 g of sodium hydroxide in 50 ml of water/50 ml of toluene are added at 10° C., the aqueous phase is washed again with toluene, the organic phases are dried and 0.85 g is obtained after crystallization from ether.

Yield: 51.2% of theory $^1$H-NMR (CDCl$_3$): δ=3.6 (s, 3H, CH$_3$); 6.5 (dd, 1H, CH-CHO); 7.0–7.5 (m, 10H, aromatic-H, CH); 9.5 (d, 1H, CHO) ppm.

EXAMPLE 6

Methyl (E)-7-[4-(4-fluorophenyl)-1-methyl-3-phenyl-4-imidazolin-2-on-5-yl]-5-hydroxy-3-oxo-hept-6-enoate

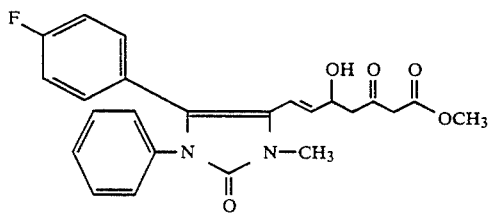

0.59 ml (5.4 mmol) of methyl acetoacetate is added dropwise under nitrogen to a suspension of 135 mg (5.6 mmol) of sodium hydride in 14 ml of tetrahydrofuran at −5° C. After 15 minutes, 4.0 ml (5.6 mmol) of 15% strength n-butyllithium in n-hexane are added dropwise at −5° C. the mixture is stirred for 15 minutes, a solution of 1.3 g (5.9 mmol) of zinc bromide in 20 ml of THF is added, the mixture is stirred for 15 minutes and a solution of 0.6 g (1.8 mmol) of the compound from Example 5 in 6 ml of tetrahydrofuran is added. After 30 minutes at −5° C., the mixture is hydrolyzed using saturated ammonium chloride solution, washed three times with dichloromethane, and the organic phase is dried and 380 mg are obtained after removing the solvent and washing the residue with petroleum ether.

Yield: 48% of theory $^1$H—NMR (CDCl$_3$): δ=2.7; 3.0 (2d, 2H, CH$_2$); 3.5 (s, 5H, NCH$_3$, CH$_2$C=O); 3.7 (s, 3H, OCH$_3$); 4.65 (br, 1H, CHOH); 5.9 (dd, 1H, CHCHO); 6.4 (d, 1H, CH); 6.9–7.4 (m, 9H, aromatic-H) ppm.

EXAMPLE 7

Methyl erythro-(E)-3,5-dihydroxy-7-[4-(4-fluorophenyl)-1-methyl-3-phenyl-4-imidazolin-2-on-5-yl]-hept-6-enoate

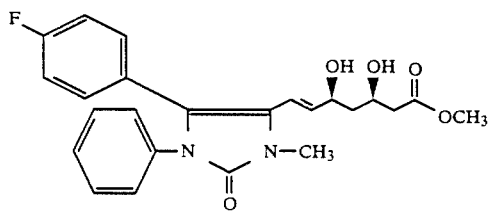

Air is blown through a solution of 350 mg (0.8 mmol) of the compound from Example 6 and 1.12 ml (1.12 mmol) of triethylborane (1M in tetrahydrofuran) in 7 ml of tetrahydrofuran for 5 minutes, 42.3 mg (1.12 mmol) of sodium borohydride and, slowly, 0.76 ml of methanol are added at −30° C., the mixture is stirred for 30 minutes at −30° C., a mixture of 3 ml of 30% strength hydrogen peroxide solution and 6.5 ml of water are added so that the temperature does not exceed 0° C., the mixture is diluted after 30 minutes with water, washed three times with ethyl acetate, the organic phase is washed with sodium hydrogen carbonate solution and dried, the solvent is removed in vacuo and 60 mg are obtained after chromatography over silica gel (ethyl acetate)

Yield: 17% of theory $^1$H-NMR (CDCl$_3$): δ=1.6 (m, 2H, CH$_2$); 2.5 (m, 2H, CH$_2$C=O); 3.4 (s, 3H, NCH$_3$); 3.7 (s, 3H, CH$_3$); 4.2 (br, 1H, CHOH); 4.4 (br, 1H, CHOH); 5.9 (dd, 1H, CHCHOH); 6.3 (d, 1H, CH); 6.8–7.5 (m, 9H, aromatic-H) ppm.

EXAMPLE 8

2-(Benzyl-isopropylamino)-1-(4-fluorophenyl)-1-oxo-1-ethane hydrochloride

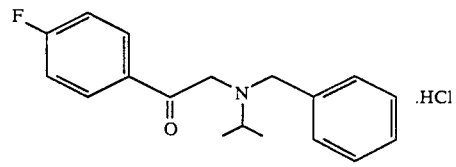

46.9 g of 2-(benzyl-isopropylamino)-1-(4-fluorophenyl)-1-oxo-1-ethane hydrochloride are obtained from 55 g (0.25 mol) of α-bromo-4-fluoroacetophenone and 78 g (0.52 mol) of isopropylbenzylamine analogously to Example 1.

Yield: 57.5% of theory $^1$H-NMR (DMSO): δ=1.4 (dd, 6H, CH$_3$); 3.8 (m, 1H, CH); 4.4 (m, 2H, CH$_2$); 5.0 (m, 2H, CH$_2$C=O); 7.2–8.0 (m, 9H, aromatic-H) ppm.

EXAMPLE 9

1-(4-Fluorophenyl)-2-isopropylamino-1-oxo-ethane hydrochloride

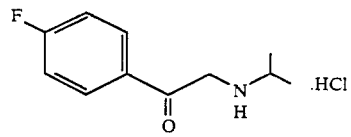

25.7 g of 1-(4-fluorophenyl)-2-isopropylamino-1-oxo-ethane hydrochloride are obtained from 44.8 g (0.14 mol) of the compound from Example 8 analogously to Example 2.

Yield: 79.8% of theory $^1$H-NMR (DMSO): δ=1.3 (d, 6H, CH$_3$); 3.4 (m, 1H, CH); 4.8 (br, 2H, CH$_2$); 7.4–8.3 (m, 4H, aromatic-H) ppm.

EXAMPLE 10

N-[2-(4-Fluorophenyl)-2-oxo-ethyl]-N-isopropyl-N'-phenylurea

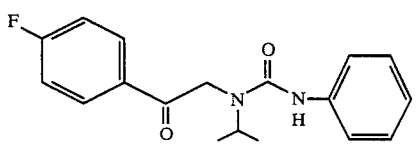

6.3 g of N-[2-(4-fluorophenyl)-2-oxo-ethyl]-N-isopropyl-N'-phenylurea are obtained from 7.0 g (30.2 mmol) of the compound from Example 9 and 3.05 g (30.2 mmol) of phenyl isocyanate analogously to Example 3.

Yield: 66.4% of theory $^1$H-NMR (CDCl$_3$): δ=1.2 (dd, 6H, CH$_3$); 2.9 (s, 1H, NH); 3.5 (dd, 2H, CH$_2$); 4.35 (m, 1H, CH); 6.9–7.6 (m, 9H, aromatic-H) ppm.

EXAMPLE 11

4-(4-Fluorophenyl)-1-isopropyl-3-phenyl-4-imidazolin-2-one

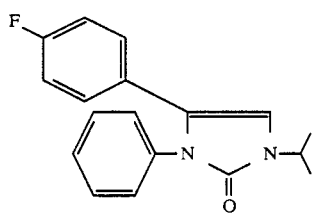

4.6 g of 4-(4-fluorophenyl)-1-isopropyl-3-phenyl-4-imidazolin-2-one are obtained from 5.3 g (16.9 mmol) of the compound from Example 10 analogously to Example 4.

Yield: 91.9% of theory $^1$H-NMR (CDCl$_3$): δ=1.4 (d, 6H, CH$_3$); 4.5 (m, 1H, CH); 6.45 (s, 1H, CH); 6.8–7.4 (m, 9H, aromatic-H) ppm.

EXAMPLE 12

(E)-3-[4-(4-Fluorophenyl)-1-isopropyl-3-phenyl-4-imidazolin-2-on-5-yl]-prop-2-enal

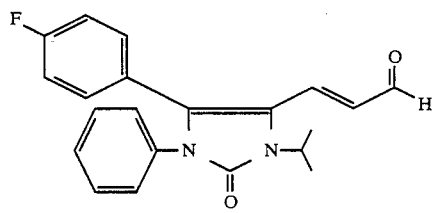

1.6 g of (E)-3-[4-(4-fluorophenyl)-1-isopropyl-3-phenyl-4-imidazolin-2-on-5-yl]-prop-2-enal are obtained from 2.0 g (6.8 mmol) of the compound from Example 11 analogously to Example 5.

Yield: 67.7% of theory $^1$H-NMR (CDCl$_3$): δ=1.6 (d, 6H, CH$_3$); 4.6 (m, 1H, CH); 6.2 (dd, 1H, CHCHO); 6.9–7.4 (m, 10H, aromatic-H, CH); 9.4 (d, 1H, CHO) ppm.

EXAMPLE 13

Methyl (E)-7-[4-(4-fluorophenyl)-1-isopropyl-3-phenyl-4-imidazolin-2-on-5-yl]-5-hydroxy-3-oxo-hept-6-enoate

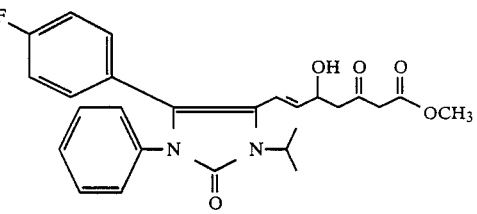

1.1 g of crude product are obtained from 0.8 g (2.3 mmol) of the compound from Example 12 analogously to Example 6. After chromatography over silica gel (dichloromethane/methanol 10:1) 0.8 g of methyl(E)-7-[4-(4-fluorophenyl)-1-isopropyl-3-phenyl-4-imidazolin-2-on-5-yl]-5-hydroxy-3-oxo-hept-6-enoate are obtained.

Yield: 75% of theory $^1$H-NMR (CDCl$_3$): δ=1.6 (d, 6H, CH$_3$); 2.7; 3.0 (2d, 2H, CH$_2$); 3.4 (s, 2H, CH$_2$); 3.75 (s, 3H, CH$_3$); 4.4 (m, 1H, CH). 4.6 (m, 1H, CH—OH); 5.6 (dd, 1H, CH); 6.4 (d, 1H, CH); 6.8–7.4 (m, 9H, aromatic-H) ppm.

EXAMPLE 14

Methyl erythro-(E)-3,5-dihydroxy-7-[4-(4-fluorophenyl)-1-isopropyl-3-phenyl-4-imidazolin-2-on-5-yl]-hept-6-enoate

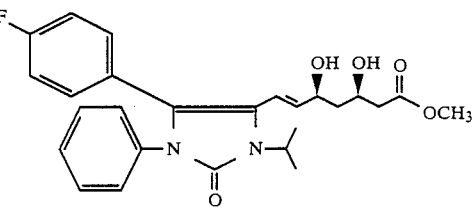

320 mg of methyl erythro-[E]-3,5-dihydroxy-7-[4-(4-fluorophenyl)-1-isopropyl-3-phenyl-4-imidazolin-2-on-5-yl]-hept-6-enoate are obtained from 0.8 g (1.7 mol) of the compound from Example 13 analogously to Example 7.

Yield: 40% of theory $^1$H-NMR (CDCl$_3$): δ=1.5 (m, 8H, CH$_3$, CH$_2$); 2.5 (m, 2H, CH$_2$); 3.7 (s, 3H, CH$_3$); 4.2; 4.4 (2m, 2H, CH); 4.5 (m, 1H, CH); 5.6 (dd, 1H, CH); 6.4 (d, 1H, CH); 6.8–7.3 (m, 9H, aromatic-H) ppm.

EXAMPLE 15

N-[2-(4-Fluorophenyl)-2-oxo-ethyl]-N-methyl-N'-phenylthiourea

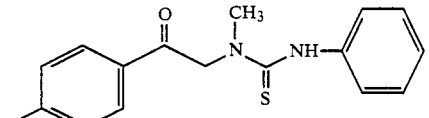

3.67 g of the abovementioned compound are obtained from 3 g (12.5 mmol) of the compound from Example 2 and 1.6 g (12.5 mmol) of phenyl isothiocyanate analogously to Example 3.

Yield: 97.2% of theory

¹H-NMR (DMSO): δ=2.3 (s, 1H); 3.35 (s, 3H); 4.0 (q, 1H); 7.0–7.6 (m, 5H) ppm.

EXAMPLE 16

4-(4-Fluorophenyl)-1-methyl-3-phenyl-4-imidazolin-2-thione

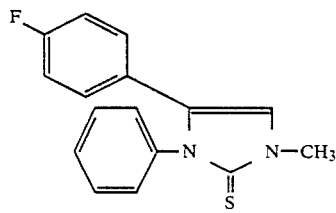

2.99 g of the abovementioned compound are obtained from 3.5 g (11.6 mmol) of the compound from Example 15 analogously to Example 4.

Yield: 91% of theory

¹H-NMR (CDCl₃): δ=3.7 (s, 3H); 6.8–7.5 (m, 10H) ppm.

EXAMPLE 17

(E)-3-[4-(4-Fluorophenyl)-1-methyl-3-phenyl-4-imidazolin-2-thion-5-yl]-prop-2-enal

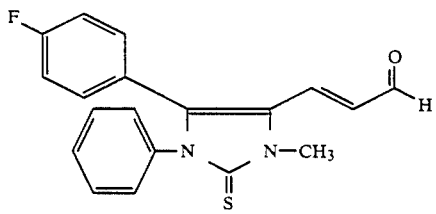

1.8 g of product are obtained from 2.4 g (8.45 mmol) of the compound from Example 16 analogously to Example 5.

Yield: 61.1% of theory

¹H—NMR (CDCl₃): δ=4.0 (s, 3H); 6.5 (dd, 1H); 6.9 (d, 1H); 6.95–7.5 (m, 9H); 9.5 (d, 1H) ppm.

EXAMPLE 18

Methyl (E)-7-[4-(4-fluorophenyl)-1-methyl-3-phenyl-4-imidazolin-2-thion-5-yl]-5-hydroxy-3-oxo-hept-6-enoate

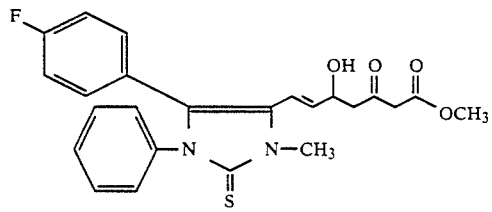

3.0 g of crude product are obtained from 1.8 g (5.3 mmol) of the compound from Example 17 analogously to Example 6.

Yield: 100% of theory

¹H—NMR (CDCl₃): δ=2.3 (s, 2H); 3.5 (s, 3H); 3.7 (s, 3H); 3.75 (s, 2H): 4.65 (m, 1H); 5.85 (dd, 1H); 5 9 (d, 1H); 6.8–7.5 (m, 9H);

EXAMPLE 19

Methyl erythro-(E)-3,5-dihydroxy-7-[4-(4-fluorophenyl)-1-methyl-3-phenyl-4-imidazolin-2-thion-5-yl]-hept-6-enoate

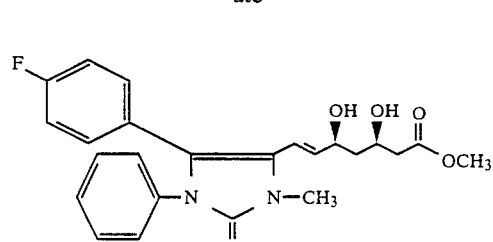

0.3 g of product is obtained from 2.11 g (4.6 mmol) of the compound from Example 18 analogously to Example 7.

Yield: 14.2% of theory

¹H—NMR (CDCl₃): δ=1.6 (m, 2H); 2.5 (d, 2H); 3.7 (s, 3H); 3.8 (s, 3H); 4.2 (m, 1H); 4.5 (m, 1H); 5.85 (dd, 1H); 5.9 (d, 1H); 6.9–7.4 (m, 9H) ppm.

EXAMPLE 20

Methyl erythro-(E)-3,5-dihydroxy-7-[4-(4-fluorophenyl)-1-isopropyl-3-phenyl-4-imidazolin-2-thion-5-yl]-hept-6-enoate

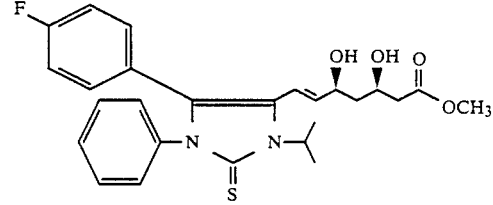

The product is obtained analogously to Example 19.

USE EXAMPLE

EXAMPLE 21

The determination of enzyme activity was carried out as modified by G. C. Ness et al., Archives of Biochemistry and biophysics 197, 493–499 (1979). Male Rico rats (body weight 300–400 g) were treated for 11 days with altromin powdered feed to which 40 g of cholestyramine/kg of feed was added. After decapitation, the liver was removed from the animals and placed on ice. The livers were comminuted and homogenized 3 times in a Potter-Elvejem homogenizer in 3 volumes of 0.1M saccharose, 0.05 M KCl, 0.04M K$_x$H$_y$ phosphate, 0.03M ethylenediaminetetraacetic acid, 0.002M dithiothreitol (SPE) buffer pH 7.2. The mixture was subsequently centrifuged at 15 000 g for 15 minutes and the sediment was discarded. The supernatant was sedimented at 100 000 g for 75 minutes. The pellet is taken up in ¼ volumes of SPE buffer, homogenized again and subsequently centrifuged at 100,000 g for 60 minutes again. The pellet is taken up using a 5-fold amount of its volume of SPE buffer, homogenized and frozen and stored at −78° C. (=enzyme solution).

For testing, the test compounds (or mevinolin as reference substance) were dissolved in dimethylformamide with the addition of 5% by volume of 1N NaOH and employed in various concentrations in the enzyme test using 10 μl. The test was started after preincubation of the compounds with the enzyme at 37° C. for 20 minutes. The test batch was 0.380 ml and contained 4 μmol of glucose-6-phosphate, 1.1 mg of bovine serum albumin, 2.1 μmol of dithiothreitol, 0.35 μmol of NADP, 1 unit of glucose-6-phosphate dehydrogenase, 35 pmol of $K_xH_y$ phosphate pH 7.2, 20 μl of enzyme preparation and 56 Nmol of 3-hydroxy-3-methyl-glutaryl coenzyme A (glutaryl-3-$^{14}$C) 100 000 dpm.

After an incubation of 60 minutes at 37° C., the batch was centrifuged and 600 μl of the supernatant was applied to a 0.7×4 cm column filled with a 5-chloride 100–200 mesh (anion exchanger). The column was washed with 2 ml of distilled water and 3 ml of a scintillation fluid were added to the running plus washing water and counted in an LKB scintillation counter. $IC_{50}$ values were determined by intrapolation by plotting the percentage inhibition against the concentration of the compound in the test. To determine the relative inhibitory potency, the $IC_{50}$ value of the reference substance mevinolin was set at 100 and compared with the simultaneously determined $IC_{50}$ value of the test compound.

The active compounds according to Examples 1 to 14 show a higher action in comparison with mevinolin, e.g. the compound of Example 14 has the relative activity of 2 (compared with mevinoline=1).

EXAMPLE 22

The subchronic action of the disubstituted pyridines on blood cholesterol values of dogs was tested in feeding experiments extending over several weeks. For this, the substance to be investigated was given p.o. once daily in a capsule to healthy beagle dogs together with the feed over a time period of several weeks. In addition, during the entire experimental period, i.e. before, during and after the administration period of the substance to be investigated, colestyramine (4 g/100 g of feed) was mixed with the feed as the gallic acid sequestrant. Twice weekly, venous blood was taken from the dogs and the serum cholesterol was determined enzymatically. The serum cholesterol values during the administration period were compared with the serum cholesterol values before the administration period (controls).

It will be understood that the specification and examples are illustrative but not limitative of the present invention and that other embodiments within the spirit and scope of the invention will suggest themselves to those skilled in the art.

We claim:

1. A substituted imidazolinone or imidazolinethione of the formula

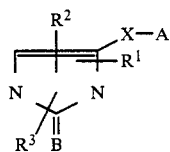

in which
R$^1$ stands for cycloalkyl, or stands for alkyl which can be substituted by halogen, cyano, alkoxy, alkylthio, alkylsulfonyl, trifluoromethyl, trifluoromethoxy, trifluoromethylthio, trifluoromethylsulfonyl, alkoxycarbonyl or acyl, or by a group of the formula —NR$^4$R$^5$, wherein R$^4$ and R$^5$ are identical and denote alkyl, aryl, aralkyl, acyl, alkylsulphonyl or arylsulphonyl, or by carbamoyl, dialkylcarbmoyl, sulphamoyl, dialkylsulphamoyl, aryl aryloxy, arylthio, arylsulphonyl, aralkoxy, aralkylthio or aralkylsulphonyl, where the aryl radicals of the lastmentioned substituents can be monosubstituted, disubstituted or trisubstituted by halogen, cyano, trifluoromethyl, trifluoromethoxy, alkyl, alkoxy, alkylthio or alkylsulphonyl, each of which is identical or different, R$^2$ stands for aryl which can be monosubstituted to pentasubstituted by alkyl, alkoxy, alkylthio, alkylsulphonyl, aryl, aryloxy, arylthio, arylsulphonyl, halogen, cyano, nitro, trifluoromethyl, trifluoromethoxy, trifluoromethylthio, alkoxyacarbonyl, sulphamoyl, dialkylsulphamoyl, carbamoyl or dialkylcarbamoyl, or by a group of the formula —Nr$^4$R$^5$, each of which is identical or different, wherein R$^4$ and R$^5$ have the abovementioned meaning.

R$^3$ stands for hydrogen or stands for cycloalkyl, or stands for alkyl which can be substituted by halogen, cyano, alkoxy, alkylthio, alkylsulphonyl, trifluoromethyl, trifluoromethoxy, trifluoromethylthio, trifluoromethoxy, trifluoromethylsulphonyl, alkoxycarbonyl or acyl, or by a group of the formula —NR$^4$R$^5$, wherein R$^4$ and R$^5$ have the abovementioned meaning, or by carbamoyl, dialkylcarbamoyl, sulphamoyl, dialkylsulphamoyl, aryl, aryloxy, arylthio, arylsylphonyl, araloxy, aralkylthio or aralkylsulphonyl, where the aryl radicals of the last-mentioned substitutents can be monosubstituted, disubstituted or trisubstituted by halogen, cyano, trifluoromethyl, trifluoromethoxy, alkyl, alkoxy, alkylthio or alkylsulphonyl, each of which is identical or different, or R$^3$ stands for aryl which can be monosubstituted to pentasubstituted by alkyl, alkoxy, alkylthio, alkylsulphonyl, aryl, aryloxy, arylthio, arylsulphonyl, araylkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl or dialkylcarbamoyl, or by a group of the formula —NR$^4$R$^5$, each of which is identical or different, wherein R$^4$ and R$^5$ have the abovementioned meaning, B stands for oxygen or sulphur, X stands for a group of the formula —CH$_2$—Ch$_2$— or —CH=CH—, R$^6$ denotes hydrogen or alkyl and R$^7$ denotes hydrogen, a methyl, aralkyl or aryl radical or a cation.

2. A substituted imidazolinone or imidazolinethione according to claim 1, in which R$^1$ stands for cyclopropyl, cyclopentyl or cyclohexyl, or stands for lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl, lower alkylcarbonyl, by a group of the formula —NR$^4$R$^5$, wherein R⁴ and R⁵ are identical or different and denote lower alkyl, phenyl, benzyl, acetyl, benzoyl, phenylsulphonyl or lower alkylsulphonyl, phenyl phenoxy, phenylthio, phenylsulphonyl, benzyloxy, benzylthio, benzylsulphonyl, phenylethoxy, phenylethylthio or phenylethylsulphonyl, where the aryl radicals mentioned can be monosubstituted or disubstituted by fluorine, chlorine, bromine, lower alkyl, lower alkoxy, trifluoromethyl, or trifluoromethoxy, each of which is identical or different, R² stands for phenyl or naphthyl which can be monosubstituted to tetrasubstituted by lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio or lower alkoxy carbonyl, or by a group of the formula —NR⁴R⁵, each of whoch is identical or different, where R⁴ and R⁵ have the abovementioned meaning, R³ stands for hydrogen, or stands for cyclopropyl, cyclopentyl or cyclohexyl or stands for lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl, lower alkylcarbonyl, by a group of the formula —NR⁴R⁵, wherein R⁴ and R⁵ have the abovementioned meaning, or by phenyl, phenoxy, phenylthio, phenylsulphonyl, benzyloxy, benzylthio, benzylsulphonyl, phenylethoxy, phenylethylthio or phenylethylsulphonyl, where the aryl radicals mentioned can be monosubstituted or disubstituted by fluorine, chlorine, bromine, lower alkyl, lower alkoxy, trifluoromethyl or trifluoromethoxy, each of which is identical or different, or R³ stands for phenyl or naphthyl which can be monosubstituted to tetrasubstituted by lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio or lower alkoxycarbonyl, or by a group of the formula —NR⁴R⁵, each of which is identical or different, where R⁴ and R⁵ have the abovementioned meaning, B stands for O or S, X stands for a group of the formula —CH₂—CH₂— or —CH=CH—, R⁶ denotes hydrogen or lower alkyl, and R⁷ denotes ($C_1$ to $C_6$), aryl ($C_6$ to $C_{12}$) or aralkyl ($C_7$ to $C_{10}$), or denotes a physiologically tolerable cation.

3. A substituted imidazolinone or imidazolinethione according to claim 1, in which R¹ stands for cyclopropyl, cyclopentyl or cyclohexyl, or stands for sec.-butyl or tert.butyl, each of which can be substituted by fluorine, chlorine, bromine, cyano, methoxy, ethoxy, propoxy, isopropoxy, butoxy, sec.butoxy, tert.butoxy, methylthio, ethylthio, propylthio, isopropylthio, methylsulphonyl, ethylsulphonyl, propylsulphonyl, isopropylsulphonyl, trifluoromethyl, trifluoromethoxy, methoxycarbonyl, ethoxycarbonyl, butoxycarbonyl, isobutoxycarbonyl, tert.butoxycarbonyl, benzoyl, acetyl, phenyl, phenoxy, phenylthio, phenylsulphonyl, benzyloxy, benzylthio or benzylsulphonyl, R² stands for phenyl which can be monosubstituted, disubstituted or trisubstituted by methyl, ethyl, propyl, isopropyl, butyl, isobutyl, tert.butyl, methoxy, ethoxy, propoxy, isopropoxy, butoxy, isobutoxy, tert.butoxy, methylthio, ethylthio, propylthio, isopropylthio, methylsulphonyl, ethylsulphonyl, propylsulphonyl, isopropylsulphonyl, phenyl, phenoxy, benzyl, benzyloxy, fluorine, chlorine, bromine, cyano, trifluoromethyl, trifluoromethoxy, methoxycarbonyl, ethoxycarbonyl, propoxycarbonyl, isopropoxycarbonyl, butoxycarbonyl, isobutoxycarbonyl or tert.butoxycarbonyl, each of which is identical or different, R³ stands for hydrogen, cyclopropyl, cyclopentyl or cyclohexyl, or stands for methyl, ethyl, propyl, isopropyl, butyl, isobutyl, tert.butyl, pentyl, isopentyl, hexyl or isohexyl which can be substituted by fluorine, chlorine, bromine, cyano, methoxy, ethoxy, propoxy isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, trifluoromethyl, trifluoromethoxy, methoxycarbonyl, ethoxycarbonyl, propoxycarbonyl, isopropoxycarbonyl, butoxycarbonyl, isobutoxycarbonyl, tert.butoxycarbonyl, benzoyl, acetyl or ethylcarbonyl, or by a group —NR⁴R⁵, where R⁴ and R⁵ are identical or different and denote methyl, ethyl, propyl, isopropyl, butyl, isobutyl, tert.butyl, phenyl, benzyl, acetyl, methylsulphonyl, ethylsulphonyl, propylsulphonyl, isopropylsulphonyl or phenylsulphonyl, or by phenoxy, phenylthio, phenylsulphonyl, benzyloxy, benzylthio or benzylsulphonyl, where the aryl radicals mentioned can be substituted by fluorine, chlorine, methyl, ethyl, propyl, isopropyl, isobutyl, tert.butyl, methoxy, ethoxy, propoxy, isopropoxy, butoxy, isobutoxy, tert.butoxy, trifluoromethyl or trifluoromethoxy, or R³ stands for phenyl which can be monosubstituted, disubstituted or trisubstituted by methyl, ethyl, propyl, isopropyl, butyl, isobutyl, tert.butyl, pentyl, isopentyl, hexyl, isohexyl, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, phenyl, phenoxy, phenylthio, phenylsulphonyl, benzyl, benzyloxy, benzylthio, benzylsulphonyl, fluorine, chlorine, bromine, cyano, trifluoromethyl, trifluoromethoxy, trifluoromethylthio, methoxycarbonyl, ethoxycarbonyl, propoxycarbonyl, isopropoxycarbonyl, butoxycarbonyl, isobutoxycarbonyl or tert.butoxycarbonyl, or by a group —NR⁴R⁵, each of which is identical or different, where R⁴ and R⁵ have the abovementioned meaning, B stands for oxygen or sulphur, X stands for a group of the formula —CH₂—CH₂— or —CH=CH—, R⁶ denotes hydrogen, methyl, ethyl, propyl, isopropyl, butyl, isobutyl or tert.butyl, and R⁷ denotes hydrogen, methyl, ethyl, propyl, isopropyl, butyl, isobutyl, tert.butyl or benzyl, or denotes a sodium, potassium, calcium, magnesium or ammonium ion.

4. A HMG-CoA reductase inhibiting composition comprising an effective amount therefor of a compound according to claim 1 and a diluent.

5. A unit dose of a composition according to claim 4 in the form of a tablet, capsule or ampule.

6. A method of inhibiting HMG-CoA reductase in a patient in need thereof which comprises administering to such patient an amount effective therefor of a compound according to claim 1.

7. A compound according to claim 1, in which
$R^1$ stands for cyclopropyl or lower alkyl,
$R^2$ stands for phenyl which can be monosubstituted, disubstituted or trisubstituted by lower alkyl, lower alkoxy, benzyloxy or fluorine,
$R^3$ stands for cycloalkyl or alkyl with up to 6 carbon atoms which may be substituted by lower alkoxy or phenyl which is optionally substituted once or twice with methyl and fluorine,
B stands for oxygen or sulphur,
X stands for a group of the formula —CH₂—CH₂— or —CH=CH—, and
$R^7$ denotes hydrogen, lower alkyl or a sodium, potassium, calcium, magnesium or ammonium ion.

8. A compound according to claim 1, in which
$R^1$ stands for cyclopropyl or isopropyl,
$R^2$ stands for phenyl which is optionally substituted up to three times by identical or different substituents from the group consisting of methyl, methoxy, benzyloxy and fluorine,
$R^3$ stands for cyclopropyl or alkyl with 1 to 4 carbon atoms which is optionally substituted by methoxy or phenyl which can be substituted up to twice by identical or different substituents from the group consisting of methyl and fluorine,
B stands for oxygen or sulphur, X stands for a group of the formula —CH₂CH₂— or —CH=CH—, and
$R^7$ denotes hydrogen, or denotes a sodium potassium, calcium, magnesium or ammonium ion.

9. A compound according to claim 1, wherein such compound is methyl erythro-(E)-3,5-hydroxy-7-[4-(4-fluorophenyl)-1-methyl-3-phenyl-4-imidazolin-2-on-5-yl]-hept-6-enoate of the formula

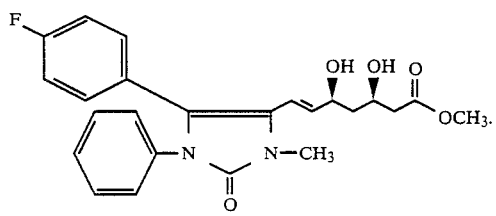

10. A compound according to claim 1, wherein such compound is methyl erythro-(E)-3,5-dihydroxy-7-[4-(4-fluorophenyl)-1-isopropyl-3-phenyl-4-imidazolin-2-on-5-yl]-hept-6-enoate of the formula

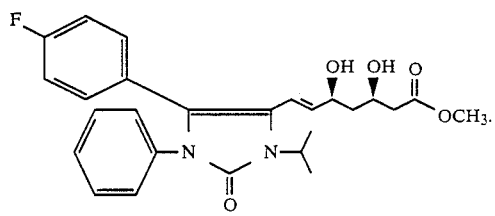

11. The method according to claim 6, wherein such compound is
methyl erythro-(E)-3,5-hydroxy-7-[4-(4-fluorophenyl)-1-methyl-3-phenyl-4-imidazolin-2-on-5-yl]-hept-6-enoate or
methyl erythro-(E)-3,5-dihydroxy-7-[4-(4-fluorophenyl) -1-methyl-3-phenyl-4-imidazolin-2-on-5-yl]-hept-3-enoate.

* * * * *

UNITED STATES PATENT AND TRADEMARK OFFICE
CERTIFICATE OF CORRECTION

PATENT NO. : 4,973,598
DATED : November 27, 1990
INVENTOR(S) : Fey et al.

It is certified that error appears in the above-identified patent and that said Letters Patent is hereby corrected as shown below:

Col. 33, claim 1 line 3   Delete " 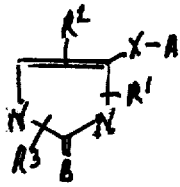 " and substitute

-- 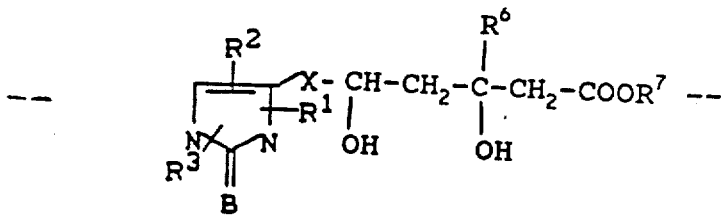 --

Col. 34, line 5    After " identical " insert -- or different --

Col. 34, line 17   After " arylsulphonyl, " insert -- aralkyl, aralkoxy, aralkylthio, aralkylsulphonyl, --

Col. 34, line 30   Delete " trifluoromethoxy "

Col. 35, line 57   After " $R^7$ denotes " insert -- alkyl --

UNITED STATES PATENT AND TRADEMARK OFFICE
CERTIFICATE OF CORRECTION

PATENT NO. : 4,973,598

DATED : November 27, 1990

INVENTOR(S) : Fey et al

It is certified that error appears in the above-identified patent and that said Letters Patent is hereby corrected as shown below:

Col. 35, line 63   After "or stands for" insert --methyl, ethyl, propyl, isopropyl, butyl,--.

Signed and Sealed this

Third Day of November, 1992

Attest:

DOUGLAS B. COMER

Attesting Officer

Acting Commissioner of Patents and Trademarks